United States Patent
Stinis

(10) Patent No.: US 9,078,993 B2
(45) Date of Patent: Jul. 14, 2015

(54) AORTIC VALVE POSITIONING SYSTEMS, DEVICES, AND METHODS

(71) Applicant: Vasular Solutions, Inc.

(72) Inventor: Curtiss T Stinis, San Diego, CA (US)

(73) Assignee: Vascular Solutions, Inc., Minneapolis, MN (US)

( * ) Notice: Subject to any disclaimer, the term of this patent is extended or adjusted under 35 U.S.C. 154(b) by 387 days.

(21) Appl. No.: 13/666,700

(22) Filed: Nov. 1, 2012

(65) Prior Publication Data

US 2013/0109960 A1    May 2, 2013

Related U.S. Application Data

(60) Provisional application No. 61/554,424, filed on Nov. 1, 2011, provisional application No. 61/590,668, filed on Jan. 25, 2012.

(51) Int. Cl.
*A61B 5/00* (2006.01)
*A61M 25/00* (2006.01)
(Continued)

(52) U.S. Cl.
CPC .......... *A61M 25/0082* (2013.01); *A61F 2/2433* (2013.01); *A61M 25/0041* (2013.01); *A61B 6/508* (2013.01); *A61F 2/2427* (2013.01); *A61F 2250/0098* (2013.01); *A61M 25/007* (2013.01);
(Continued)

(58) Field of Classification Search
CPC ....... A61F 2/24; A61F 2/2427; A61F 2/2472; A61B 19/5244; A61B 2019/5287; A61B 19/54; A61B 2019/5466
See application file for complete search history.

(56) References Cited

U.S. PATENT DOCUMENTS

| 4,747,840 A | 5/1988 | Ladika et al. |
| 6,063,082 A | 5/2000 | DeVore et al. |

(Continued)

FOREIGN PATENT DOCUMENTS

| EP | 2779944 A2 | 9/2014 |
| WO | WO-96/17644 A1 | 6/1996 |

(Continued)

OTHER PUBLICATIONS

"International Application Serial No. PCT/US2012/063082, International Search Report mailed May 13, 2013", 7 pgs.

(Continued)

*Primary Examiner* — Parikha Mehta
(74) *Attorney, Agent, or Firm* — Schwegman Lundberg & Woessner, P.A.

(57) ABSTRACT

Systems, devices, and methods for locating a geometric plane within a patient's vasculature, for example, an entry plane to a valve, are disclosed. In one example, a medical device can include a body member and an expandable element. The body member can extend along a longitudinal axis of the medical device and at least partially define a lumen. The body member can include at least one opening disposed in fluid communication with the lumen. The expandable element can include at least two radiographic markers and can be movable between at least a first configuration and a second configuration. The at least two radiographic markers can be disposed within the lumen when the expandable element is in the first configuration. The at least two radiographic members can be disposed outside of the lumen and can be radially offset from the longitudinal axis when the expandable element is in the second configuration.

22 Claims, 10 Drawing Sheets

(51) Int. Cl.
  *A61F 2/24* (2006.01)
  *A61M 25/01* (2006.01)
  *A61M 31/00* (2006.01)
  *A61B 6/00* (2006.01)

(52) U.S. Cl.
  CPC ........ *A61M 25/0108* (2013.01); *A61M 25/0136* (2013.01); *A61M 31/005* (2013.01)

(56) References Cited

U.S. PATENT DOCUMENTS

| | | |
|---|---|---|
| 7,004,176 B2 | 2/2006 | Lau |
| 2003/0199768 A1* | 10/2003 | Cespedes et al. ............ 600/473 |
| 2004/0167619 A1* | 8/2004 | Case et al. .................. 623/1.34 |
| 2006/0020333 A1 | 1/2006 | Lashinski et al. |
| 2006/0052867 A1* | 3/2006 | Revuelta et al. ............ 623/2.18 |
| 2007/0010844 A1 | 1/2007 | Gong et al. |
| 2007/0067022 A1 | 3/2007 | Case et al. |
| 2008/0091261 A1* | 4/2008 | Long et al. ................... 623/1.24 |
| 2010/0121436 A1* | 5/2010 | Tuval et al. .................. 623/2.17 |
| 2011/0202128 A1* | 8/2011 | Duffy ........................... 623/2.11 |
| 2012/0158129 A1* | 6/2012 | Duffy et al. .................. 623/2.11 |
| 2013/0073032 A1* | 3/2013 | Wang ........................... 623/2.11 |

FOREIGN PATENT DOCUMENTS

| | | |
|---|---|---|
| WO | WO-2011/109813 A2 | 9/2001 |
| WO | WO-2013067194 A3 | 5/2013 |

OTHER PUBLICATIONS

"International Application Serial No. PCT/US2012/063082, Written Opinion mailed May 13, 2013", 8 pgs.

"European Application Serial No. 12791354.9 Response filed Mar. 5, 2015 to Office Action mailed Aug. 26, 2014", 12 pgs.

"European Application Serail No. 12791354.9, Office Action mailed Aug. 26, 2014", 2 pgs.

"International Application Serial No. PCT/US2012/063082, Response filed Aug. 6, 2013 to Written Opinion mailed May 13, 2013", 17 pgs.

"International Application Serial No. PCT/US2012/063082, International Preliminary Report on Patentability mailed Feb. 7, 2014", 8 pgs.

"International Application Serial No. PCT/US2012/063082, Written Opinion mailed Nov. 12, 2013", 7 pgs.

* cited by examiner

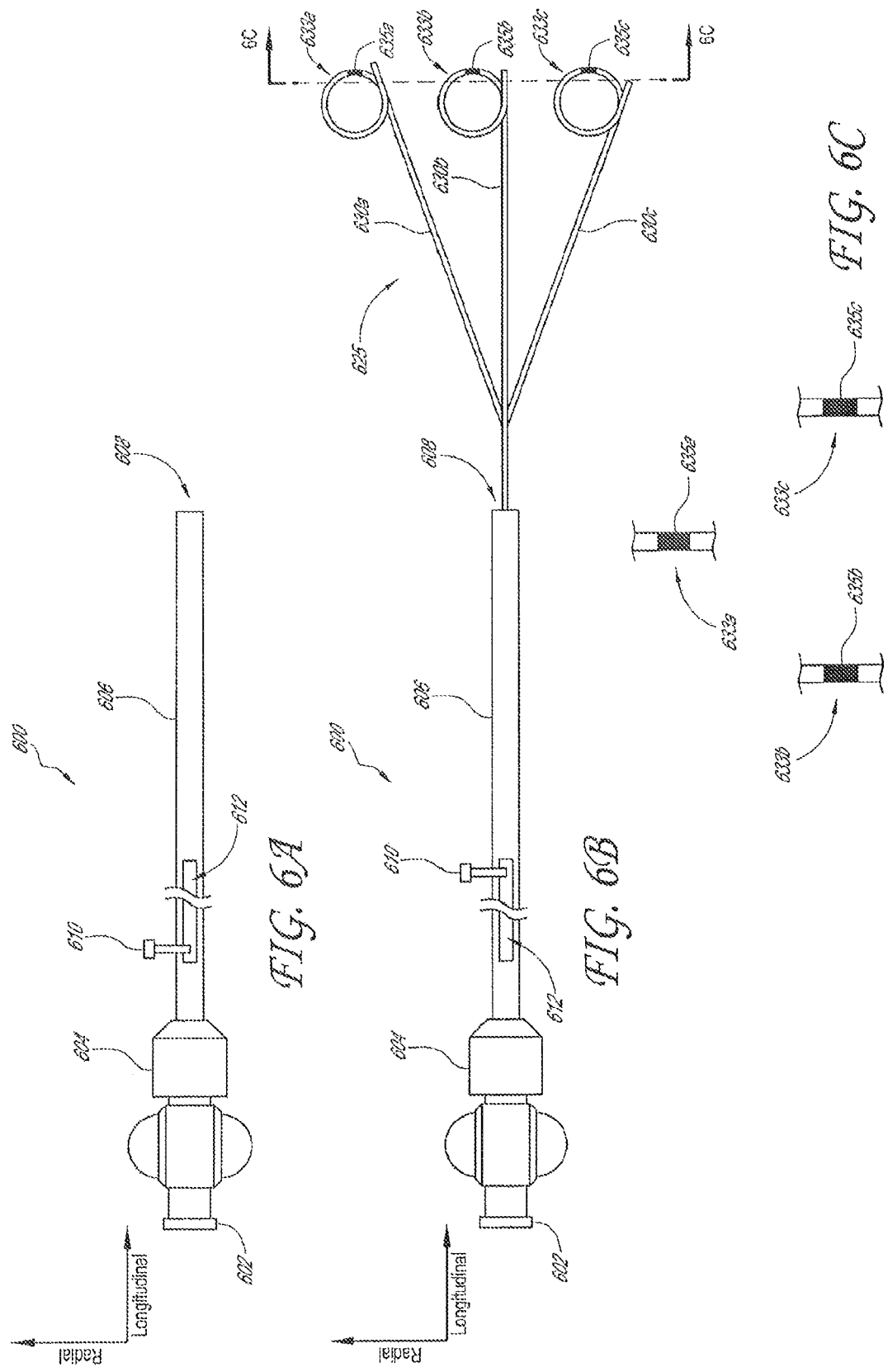

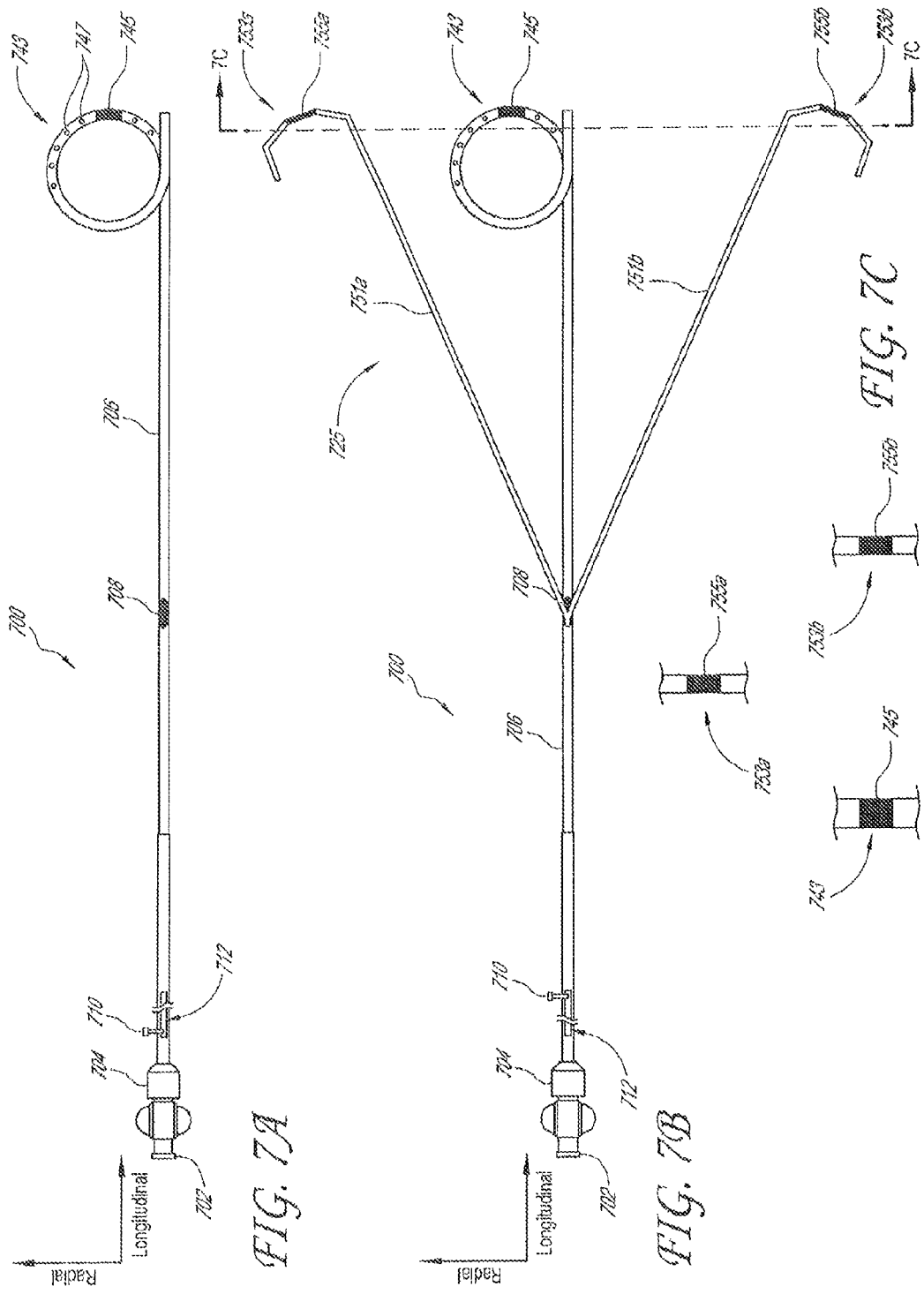

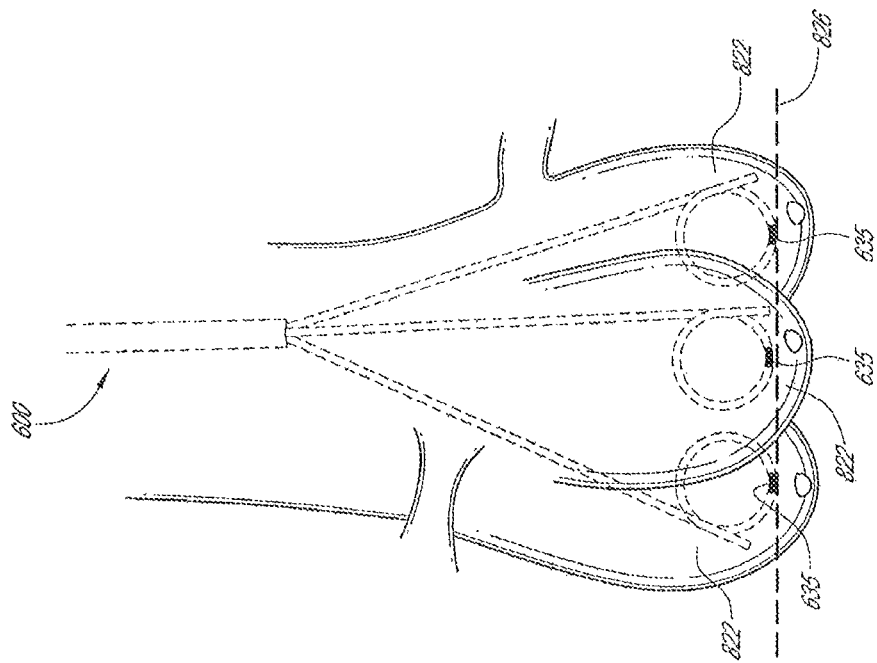
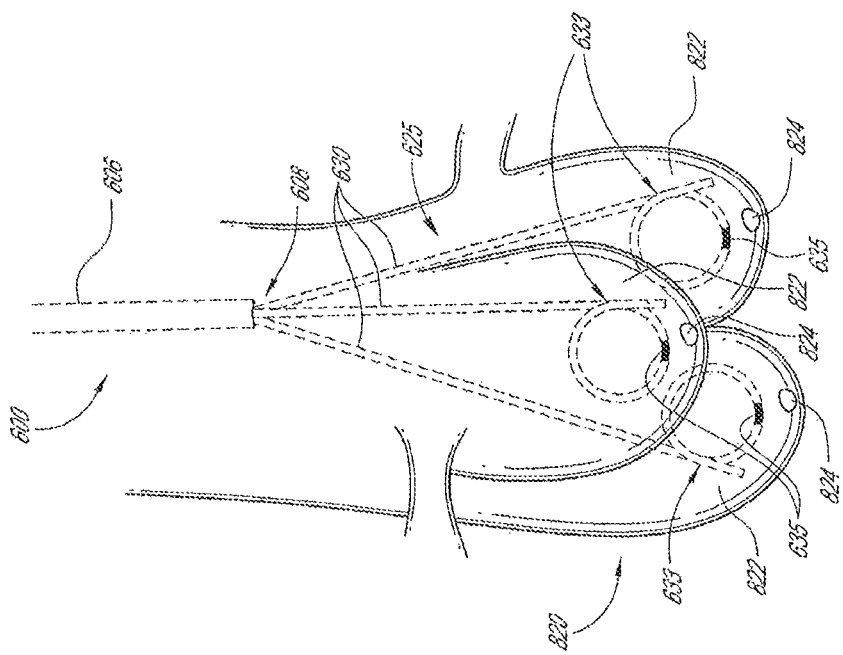

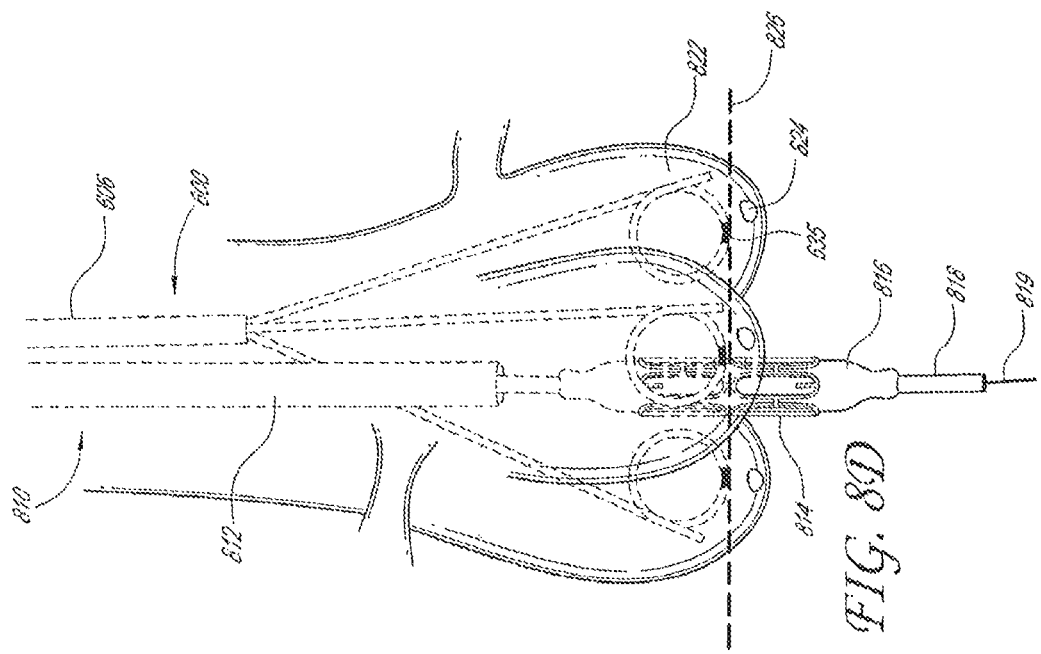
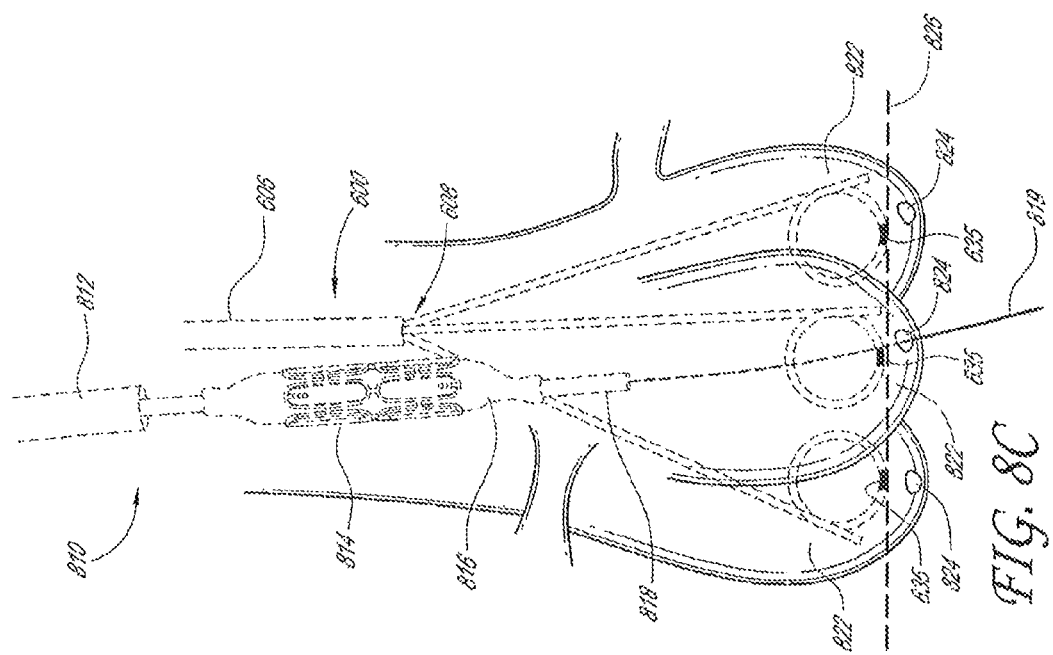

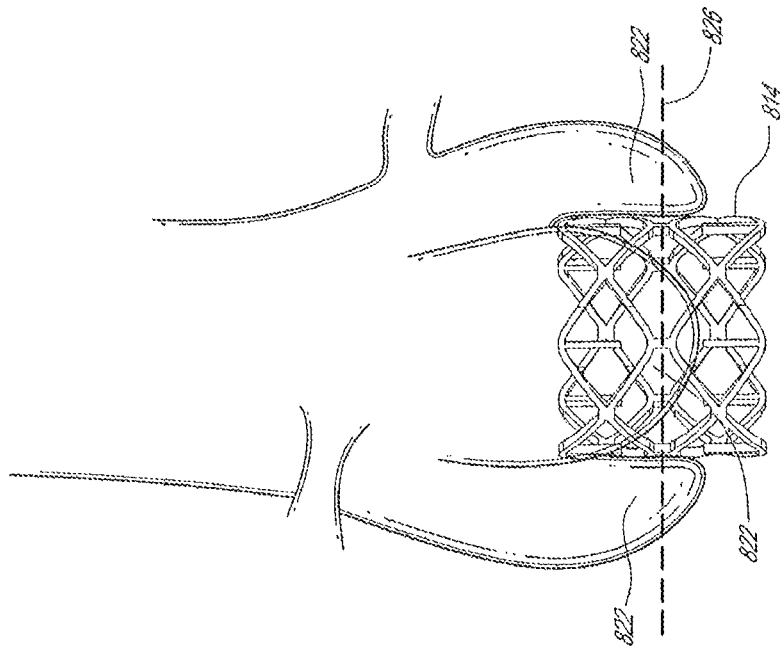
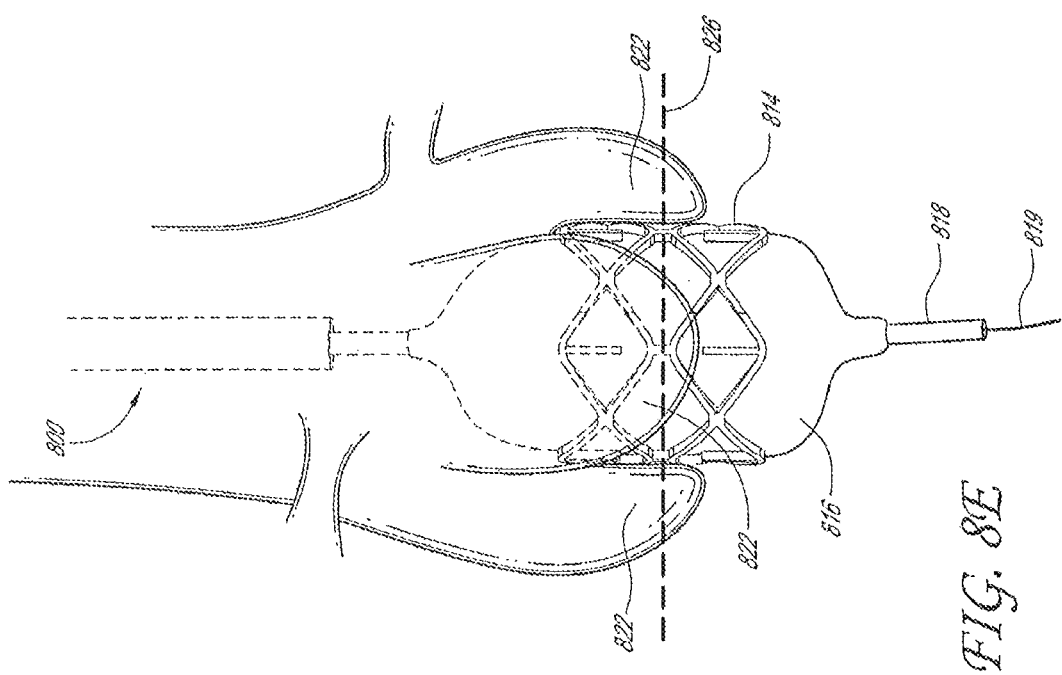
FIG. 8F
FIG. 8E

AORTIC VALVE POSITIONING SYSTEMS, DEVICES, AND METHODS

CLAIM OF PRIORITY

This non-provisional patent application claims the benefit of priority under 35 U.S.C. §119(e) to U.S. Provisional Patent Application Ser. No. 61/554,424, entitled "AORTIC VALVE POSITIONING SYSTEMS, DEVICES, AND METHODS," filed on Nov. 1, 2011, and U.S. Provisional Patent Application Ser. No. 61/590,668, entitled "AORTIC VALVE POSITIONING SYSTEMS, DEVICES, AND METHODS," filed on Jan. 25, 2012, which are hereby incorporated by reference in their entirety.

TECHNICAL FIELD

This patent document relates generally to systems, devices, and methods for positioning an aortic valve prosthesis relative to an aortic root. More specifically, but not by way of limitation, this patent document relates to systems, devices, and methods that can be implemented to position an aortic valve prosthesis relative to the cusps of a heart valve, for example, an aortic valve.

BACKGROUND

Aortic valve disease can be treated by surgically repairing a diseased valve or by replacing the diseased valve with an alternative valve, for example, a biological tissue valve and/or an aortic valve prosthesis. Surgically repairing or replacing a diseased valve can involve open heart surgery. In some situations, a diseased valve can be replaced using a transvascular procedure (e.g., a trans-catheter procedure).

OVERVIEW

The aortic valve positioning systems, devices, and methods disclosed herein each have several features or aspects, no single one of which is solely responsible for their desirable attributes. Without limiting the scope of the claims, some prominent features will now be briefly discussed. Numerous other embodiments are also contemplated, including embodiments that have fewer, additional, and/or different components, steps, features, objects, benefits, and advantages. The components, aspects, and steps can also be arranged and ordered differently. After considering this discussion, and particularly after reading the section entitled "Detailed Description of Certain Embodiments," one will understand how the features of the systems, devices, and methods disclosed herein provide advantages over known systems, devices, and methods.

In one embodiment, a medical device having a longitudinal axis is disclosed. The medical device can include, for example, a body member and an expandable element (e.g., a deployable element). The body member can extend along the longitudinal axis and at least partially define a lumen having at least one opening disposed in fluid communication with the lumen. The expandable element can include at least two radiographic markers and can be movable between at least a first configuration and a second configuration. The at least two radiographic markers can be disposed within the lumen when the expandable element is in the first configuration. The at least two radiographic markers can be disposed outside of the lumen and radially offset from the longitudinal axis when the expandable element is in the second configuration. The at least two radiographic markers can pass through the at least one opening when the expandable element moves between the first configuration and the second configuration. In one aspect, the medical device can be provided with an aortic valve prosthesis, for example, a SAPIEN transcatheter aortic valve available commercially from Edwards Lifesciences or a COREVALVE transcatheter aortic valve available commercially from Medtronic, as part of a system.

In another embodiment, a method can comprise introducing at least three radiographic markers into a patient's vasculature. The at least three radiographic markers can define a geometric plane. The method can also comprise manipulating a radiographic imaging device configured to produce a radiographic image. The radiographic imaging device can be manipulated until a produced image displays the at least three radiographic markers disposed in a common line segment, which can be indicative of at least one dimension of the geometric plane defined by the at least three radiographic markers.

To better illustrate the aortic valve positioning systems, devices, and methods disclosed herein, a non-limiting list of examples is provided here:

In Embodiment 1, a medical device comprises a body member extending along a longitudinal axis and an expandable element including at least two radiographic markers. The body member at least partially defines a lumen and has an opening disposed in communication with the lumen. The expandable element is movable between at least a first configuration, in which the at least two radiographic markers are disposed within the lumen, and a second configuration, in which the at least two radiographic markers are disposed outside of the lumen and are radially offset from the longitudinal axis. The at least two radiographic markers pass through the opening when the expandable element moves between the first configuration and the second configuration.

In Embodiment 2, the medical device of claim 1 is optionally configured such that the expandable element includes three radiographic markers.

In Embodiment 3, the medical device of claim 2 is optionally configured such that the three radiographic markers are equally radially offset from the longitudinal axis and/or equally longitudinally spaced from the opening of the body member when the expandable element is at the second configuration.

In Embodiment 4, the medical device of any one or any combination of Embodiments 2 and 3 is optionally configured such that the three radiographic markers define a geometric plane when the expandable element is at the second configuration.

In Embodiment 5, the medical device of any one or any combination of Embodiments 2-4 is optionally configured such that the expandable element includes three members, with each member coupled to or including a radiographic marker.

In Embodiment 6, the medical device of Embodiment 5 is optionally configured such that each radiographic marker is disposed on a tip portion of a member.

In Embodiment 7, the medical device of Embodiment 6 is optionally configured such that each tip portion is sized and shaped to complement, and be received by, an aortic valve cusp.

In Embodiment 8, the medical device of Embodiment 7 is optionally configured such that at least one tip portion includes a pigtail shape or a J-shape.

In Embodiment 9, the medical device of any one or any combination of Embodiments 1-8 is optionally configured such that the body member includes a tip portion and the opening is longitudinally offset along the body member from the tip portion.

In Embodiment 10, the medical device of Embodiment 9 optionally further comprises a radiographic marker coupled to or integrated with the tip portion.

In Embodiment 11, the medical device of Embodiment 10 is optionally configured such that the expandable element includes two members. Each member is coupled to or includes a radiographic marker at an end portion.

In Embodiment 12, the medical device of Embodiment 11 is optionally configured such that the radiographic markers of the expandable element and the radiographic marker of the tip portion are equally radially offset from the longitudinal axis when the expandable element is at the second configuration.

In Embodiment 13, the medical device of any one or any combination of Embodiments 11 and 12 is optionally configured such that the radiographic markers of the expandable element and the radiographic marker of the tip portion define a geometric plane when the expandable element is at the second configuration.

In Embodiment 14, the medical device of any one or any combination of Embodiments 11-13 is optionally configured such that the tip portion and the end portions are sized and shaped to complement, and be received by, an aortic valve cusp.

In Embodiment 15, the medical device of Embodiment 14 is optionally configured such that at least one of the tip portion and the end portions includes a pigtail shape or a J-shape.

In Embodiment 16, the medical device of any one or any combination of Embodiments 9-15 is optionally configured such that the tip portion includes at least one port disposed in fluid communication with the lumen.

In Embodiment 17, a system comprises the medical device of any one or any combination of Embodiments 1-16 and an aortic valve prosthesis.

In Embodiment 18, a method comprises introducing at least three radiographic markers into a vessel; advancing the at least three radiographic markers to a target location in the vessel; defining a geometric plane at the target location using the at least three radiographic markers; and manipulating a radiographic imaging device, configured to produce a radiographic image, including producing a radiographic image in which the at least three radiographic markers are disposed in a common line segment.

In Embodiment 19, the method of Embodiment 18 is optionally configured such that advancing the at least three radiographic markers to the target location includes moving an expandable element from a first configuration, in which at least two of the radiographic markers are disposed within a body member lumen, and a second configuration, in which the at least two of the radiographic markers are disposed outside of the body member lumen.

In Embodiment 20, the method of any one or any combination of Embodiments 18 or 19 is optionally configured such that defining the geometric plane at the target location includes disposing each radiographic marker proximal to a nadir of an aortic cusp in a patient.

In Embodiment 21, the method of any one or any combination of Embodiments 18-20 is optionally configured such that providing the radiographic image in which the at least three radiographic markers are disposed in the common line segment includes identifying at least one dimension of the geometric plane.

In Embodiment 22, the method of any one or any combination of Embodiments 18-21 optionally further comprises advancing an aortic valve prosthesis through the vessel and positioning the aortic valve prosthesis adjacent the target location.

In Embodiment 23, the method of Embodiment 22 is optionally configured such that positioning the aortic valve prosthesis includes positioning a first portion of the aortic valve prosthesis on a first side of the geometric plane and positioning a second portion of the aortic valve prosthesis on a second side of the geometric plane, which is opposite to the first side.

In Embodiment 24, the method of Embodiment 23 is optionally configured such that positioning the first portion of the aortic valve prosthesis on the first side of the geometric plane includes positioning between 30% and 70% of the longitudinal length of the aortic valve prosthesis on the first side of the geometric plane.

In Embodiment 25, the method of Embodiment 23 is optionally configured such that positioning the first portion of the aortic valve prosthesis on the first side of the geometric plane includes positioning between 40% and 60% of the longitudinal length of the aortic valve prosthesis on the first side of the geometric plane.

In Embodiment 26, the method of Embodiment 23 is optionally configured such that positioning the first portion of the aortic valve prosthesis on the first side of the geometric plane includes positioning between 45% and 55% of the longitudinal length of the aortic valve prosthesis on the first side of the geometric plane.

In Embodiment 27, a catheter comprises an expandable element including three pigtail-shaped catheter ends or two J-shaped Nitinol flexible wire tips.

In Embodiment 28, a catheter is configured such that, when in a deployed state, three elements form a triangular shape. A distal tip of each element is located in the same horizontal plane and equidistant from a fixed point on a main catheter body.

In Embodiment 29, a catheter comprises three rounded or J-shaped elements. Each element includes a radiographic marker located within a distal-most portion.

In Embodiment 30, a catheter comprises three extendable elements, which are rounded or J-shaped, and is flexible such that rotational manipulation by an operator will result in tips of the extendable elements sitting in direct contact with the nadirs of each of the sinuses of Valsalva.

In Embodiment 31, a catheter comprises three elements designed to be placed from above the aortic valve. The three elements can be used to precisely localize a horizontal plane of the nadirs of all three sinuses of Valsalva and allow for the injection of a contrast material.

In Embodiment 32, a catheter comprises three elements designed to
precisely localize a horizontal plane of the nadirs of all three sinuses of Valsalva of the aortic valve. The three elements can be left in place while a transvascular aortic valve prosthesis is appropriately positioned for deployment either from a femoral or a trans-apical approach.

In Embodiment 33, a catheter comprises a body member extending along a longitudinal axis and an expandable element including at least two radiographic markers. The body member at least partially defines a lumen and has an opening disposed in communication with the lumen. The expandable element is movable between at least a first configuration, in which the at least two radiographic markers are disposed within the lumen, and a second configuration, in which the at least two radiographic markers are disposed outside of the lumen and are radially offset from the longitudinal axis. The at least two radiographic markers pass through the opening when the expandable element moves between the first configuration and the second configuration.

In Embodiment 34, the catheter of Embodiment 33 is optionally configured such that the expandable element comprises three members. Each member includes a radiographic marker.

In Embodiment 35, the catheter of Embodiment 34 is optionally configured such that each member includes a distal end having a pigtail shape or a blunt tip.

In Embodiment 36, the catheter of Embodiment 34 is optionally configured such that the three members include three pigtail-shaped catheter ends or two J-shaped Nitinol flexible wire tips.

In Embodiment 37, the catheter of any one or any combination of Embodiments 34-36 is optionally configured such that the expandable element in the second configuration forms a triangular shape, with the distal tips of each member being located in the same horizontal plane and equidistant from a fixed point on the body member.

In Embodiment 38, the aortic valve positioning system, device, or method of any one (or portion of one) or any combination of Embodiments 1-37 is optionally configured such that all elements or options recited are available to use or select from.

These and other examples and features of the present aortic valve positioning systems, devices, or methods will be set forth in part in the following Detailed Description of Certain Embodiments. This Overview is intended to provide non-limiting examples of the present subject matter—it is not intended to provide an exclusive or exhaustive explanation. The Detailed Description of Certain Embodiments below is included to provide further information about the present aortic valve positioning systems, devices, and methods.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

FIGS. 6A-6C schematically depict an example of a medical device for use in visually determining a location of an entry plane of an aortic root, as constructed in accordance with at least one embodiment.

FIGS. 7A-7C schematically depict an example of a medical device for use in visually determining a location of an entry plane of an aortic root, as constructed in accordance with at least one embodiment.

FIGS. 8A-8F schematically depict an example process of positioning an aortic valve prosthesis relative to the aortic root of FIGS. 5A-5C using the medical device of FIGS. 6A-6C.

DETAILED DESCRIPTION OF CERTAIN EMBODIMENTS

Figure 1:
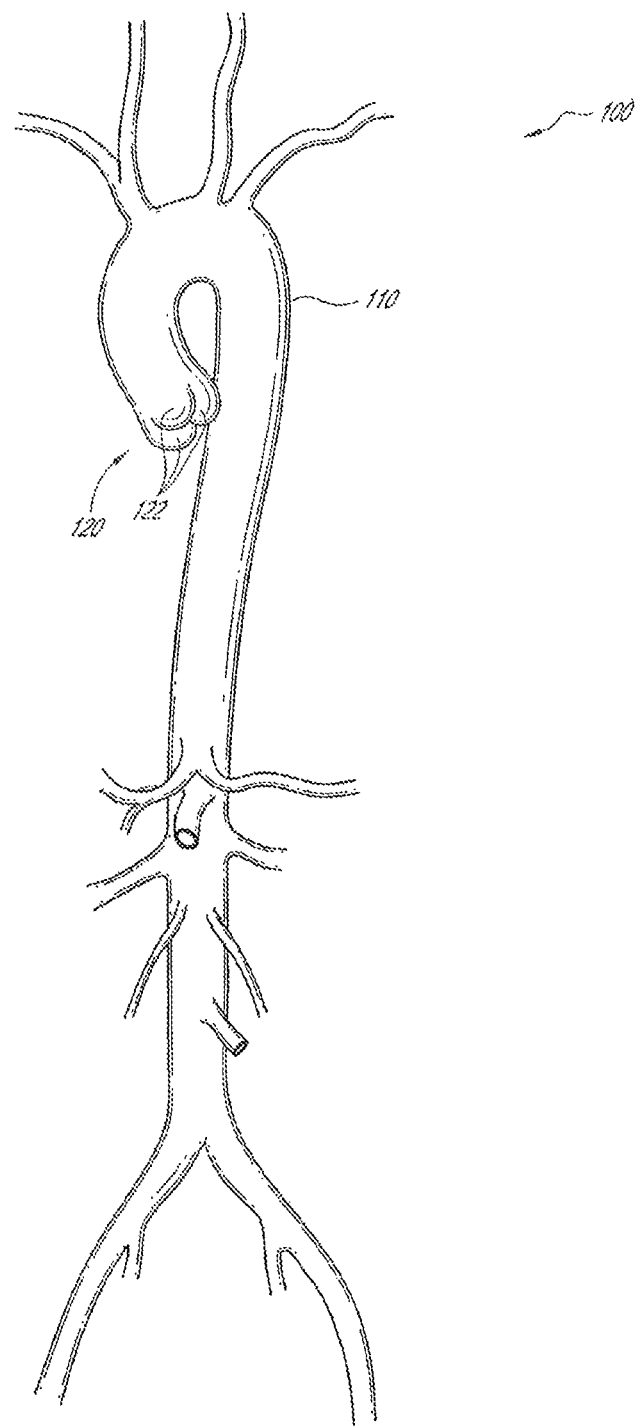
FIG. 1 schematically depicts an example of a portion of a patient's vasculature, including an aortic root and an ascending aorta.

In the following Detailed Description of Certain Embodiments, reference is made to the accompanying drawings, which form a part hereof. In the drawings, similar symbols typically identify similar components, unless context dictates otherwise. The illustrative embodiments described in the Detailed Description of Certain Embodiment, drawings, and claims are not meant to be limiting. Other embodiments can be utilized, and other changes can be made, without departing from the spirit or scope of the subject matter presented herein. It will be readily understood that the aspects and feature of the present disclosure, as generally described herein, and illustrated in the drawings, can be arranged, substituted, combined, and designed in a wide variety of different configurations, all of which are explicitly contemplated and make part of this disclosure.

FIG. 1 schematically depicts an example of a portion of a human's vasculature 100. The illustrated portion of the patient's vasculature 100 includes an aortic root 120 and an ascending aorta 110. Typically, the aortic root 120 is disposed between the left ventricle of a human heart (not shown) and the ascending aorta 110, which distributes oxygenated blood from the heart to all parts of the body through the vasculature 100. The aortic root 120 includes three cusps or sinuses 122 (e.g., the sinuses of Valsalva), for example, which collectively form the aortic valve of the human (e.g., a tricuspid valve). In some humans, the aortic root 120 can include only two cusps 122 and an aortic valve formed by only two cusps 122 can be considered a bi-cuspid valve. Although, a tri-cuspid valve generally will be depicted and treated herein, it should be understood that the systems, devices, and methods disclosed herein can be applied to bi-cuspid valves as well, for example by configuring the systems, devices, and methods for use with two cusps. It should also be understood that although the present disclosure discusses human hearts, other mammalian aortas can be of similar construction and the present invention is not limited to human use and can apply to veterinary uses.

Figure 2A:
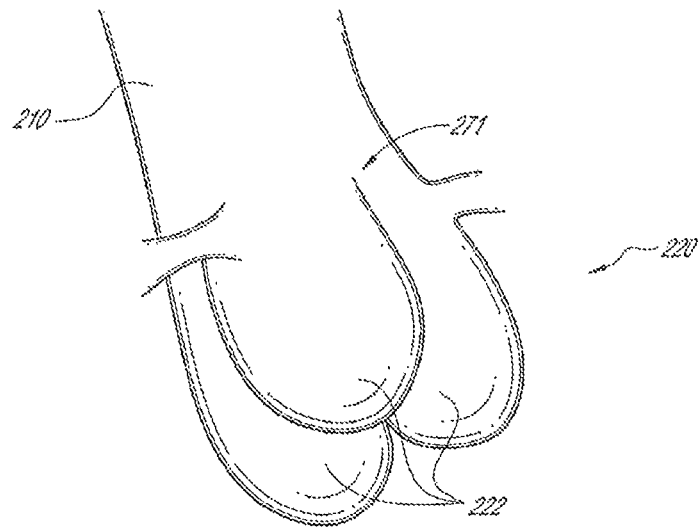
FIG. 2A schematically depicts an example of an aortic root.
Figure 2B:
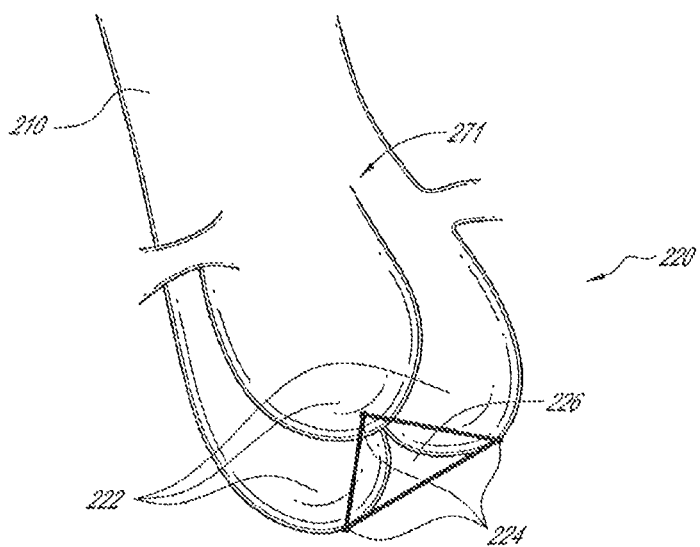
FIG. 2B schematically depicts a plane defined by the nadirs of cusps of the example aortic root of FIG. 2A.

FIGS. 2A and 2B schematically depict an example of an aortic root 220 connected to an ascending aorta 210. As shown, the aortic root 220 splits or separates from the ascending aorta 210 at a sinotubular junction 271. The cusps 222 of the aortic root 220 can extend away from the sinotubular junction toward the left ventricle of the heart (not shown). As shown in FIG. 2B, each cusp 222 can be similarly sized and shaped. In this way, and because each cusp 222 extends from the sinotubular junction 271 in the same direction, the lowest points or nadirs 224 (e.g., the most distal points from the sinotubular junction 271) of all three cusps 222 can collectively define a geometric plane 226. Although graphically illustrated as a triangle, those having ordinary skill in the art will understand that the geometric plane 226 is a two-dimensional surface extending infinitely in both dimensions with each nadir 224 being disposed on the surface. The geometric plane 226 can be considered the entry plane to the aortic root 220, because blood passes through the geometric plane 226 when the cusps 226 are in an open configuration, as discussed below.

Figure 3:
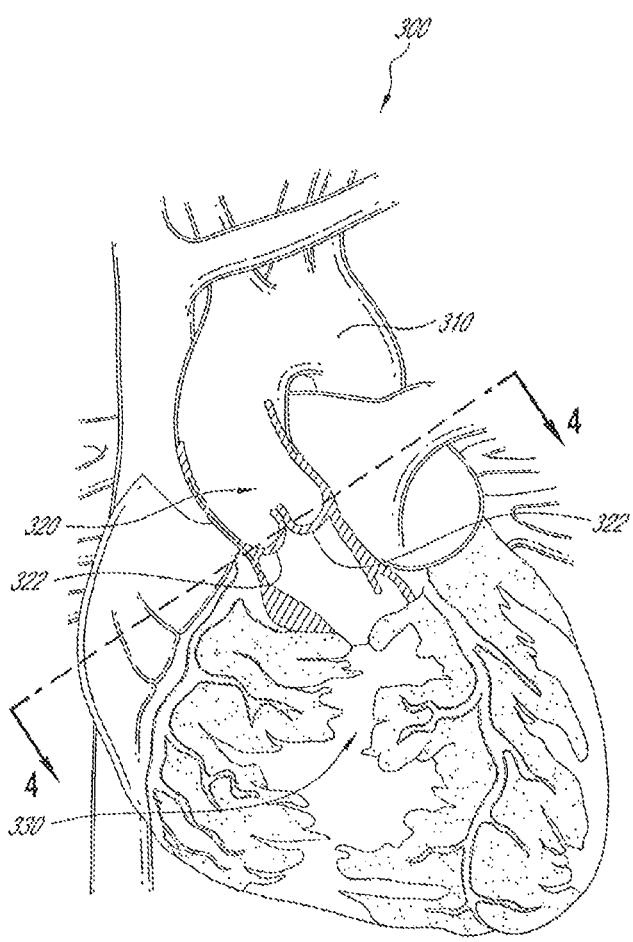
FIG. 3 schematically depicts an example of a heart including an aortic root.

Turning now to FIG. 3, an example of a heart 300 is schematically depicted. The heart 300 includes a left ventricle 330 that is fluidly coupled to an ascending aorta 310 via an aortic root 320. The aortic root 320 includes a plurality of cusps 322, for example, three cusps (two of which are visibly depicted), which collectively form a passive valve (e.g., an aortic valve) between the left ventricle 330 and the ascending aorta 310. In this way, the cusps 322 can regulate the flow of blood between the left ventricle 330 and the ascending aorta 310 in conjunction with the beating or periodic contraction of the heart 300.

Figure 4A:
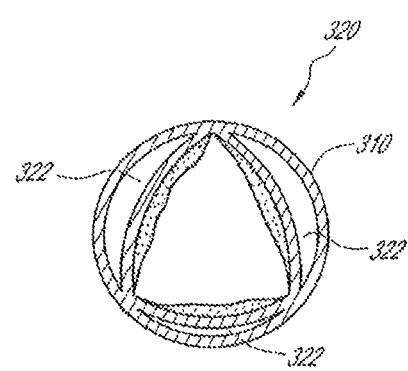
FIG. 4A schematically depicts a cross-sectional view of the aortic root of FIG. 3 taken along line 4-4 when the aortic valve is in an open configuration.

During ventricular systole, fluid pressure (e.g., the fluidic pressure of blood) rises in the left ventricle 330. After the pressure in the left ventricle 330 rises above the pressure in the ascending aorta 310, the cusps 322 of the aortic valve open so as to allow blood to exit the left ventricle 330 and flow into the aorta 310. FIG. 4A schematically illustrates a cross-sectional view of the aortic root 320 of FIG. 3 taken along line 4-4 when the cusps 322 are in the open configuration so as to allow blood to flow in between the cusps, through the aortic root 320.

Figure 4B:
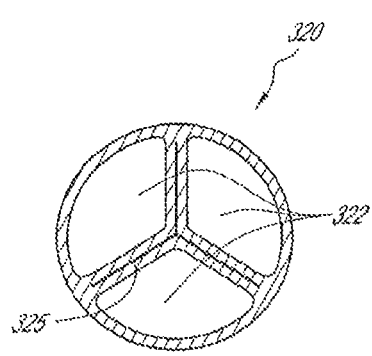
FIG. 4B schematically depicts a cross-sectional view of the aortic root of FIG. 3 taken along line 4-4 when the aortic valve is in a closed configuration.

When ventricular systole ends and ventricular diastole begins, pressure in the left ventricle 330 rapidly drops and the greater fluidic pressure in the ascending aorta 310 forces the cusps 322 of the aortic valve to close. FIG. 4B schematically illustrates a cross-sectional view of the aortic root 320 of FIG. 3 taken along line 4-4 when the cusps 322 are in the closed configuration so as to prevent, or at least inhibit, the flow of blood through the aortic root 320. When in the closed configuration, the nadirs of each cusp 322 can define a coaptation plane 325 (e.g., a plane where the edges of the cusps 322 join to seal the ascending aorta 310 from the left ventricle 330).

In some humans, the aortic valve formed by the aortic cusps or sinuses Valsalva can become diseased. Examples of aortic valve disease include aortic valve steno sis and aortic insufficiency. Aortic valve steno sis is a disease in which the opening of the aortic valve is narrowed. Such narrowing can be caused, for example, by progressive calcification of the valve and/or by acute rheumatic fever. Aortic insufficiency, sometimes referred to as aortic regurgitation, is a disease in which the aortic valve is incompetent and a volume of blood passively flows back into the left ventricle from the aorta in the wrong direction. Aortic stenosis and aortic insufficiency can co-exist and be present in parallel.

Aortic valve disease can be treated by surgically repairing a diseased valve or by replacing the diseased valve with an alternative valve, for example, a biological tissue valve or an aortic valve prosthesis. Surgically repairing or replacing a diseased valve can involve open heart surgery. Open heart surgery includes the opening of the patient's heart, which can require the stopping of the heart, and other invasive measures (e.g., the opening of the patient's chest).

In some instances, aortic valve disease can be treated by replacing a diseased valve with an aortic valve prosthesis using a transvascular procedure (e.g., a trans-catheter procedure). One such type of transvascular procedure is a transvascular aortic valve replacement (TAVR) where an aortic valve prosthesis can be inserted within an existing diseased aortic valve via a catheter. TAVR procedures can be minimally invasive as compared with open heart surgeries. For example, instead of opening the patient's chest, the aortic valve prosthesis (e.g., the replacement valve) can be passed retrograde up the aorta from an entry site in a common femoral artery or can be positioned by directly puncturing the apex of the left ventricle of the heart (e.g., trans-apical access). Accordingly, such procedures can provide several advantages over other more invasive procedures (e.g., open heart surgery).

Examples of suitable aortic valve prostheses that can be used in TAVR procedures include the SAPIEN transcatheter aortic valve available commercially from Edwards Lifesciences and the COREVALVE transcatheter aortic valve available commercially from Medtronic. The SAPIEN transcatheter aortic valve includes a self-expanding valve prosthesis having a nickel-titanium frame with a tri-cuspid valve fashioned out of porcine pericardium mounted within. The COREVALVE transcatheter aortic valve includes a balloon-expandable tubular metal stent with a tri-cuspid valve fashioned out of bovine pericardium mounted within.

One of the critical steps in performing a TAVR procedure is positioning the valve prosthesis in the appropriate location within the aortic root relative to the existing aortic valve (e.g., relative to the cusps of the aortic valve). Currently, the positioning process involves the use of multiple angiographic projections that are typically obtained via injection of iodinated contrast material to determine the optimal radiographic projection for valve deployment within the aortic valve. However, this process is difficult and can be inexact. Additionally, this process often leads to excessive use of contrast material and excessive x-ray exposure for the patient.

Other methods for obtaining an appropriate radiographic projection for valve prosthesis deployment include using computer software. Computer software methods also require several contrast material injections to determine an appropriate view via interpolation. Further, existing software packages are expensive and merely recommend a radiographic view based on interpolation, which may be subject to error. The present disclosure describes unique systems, devices, and methods that allow for radiographic visualization of the true entry plane of the aortic valve using little or no contrast media and minimal x-ray exposure. In this way, the visualization of the true entry plane (e.g., the geometric plane including the nadirs of each cusp when the aortic valve is in the open configuration) can provide a reference for properly positioning an aortic valve prosthesis relative to the aortic root during a medical procedure.

Without being limited thereto, it is generally believed that for implantation of a transvascular aortic valve prosthesis (e.g., a replacement valve used in a TAVR procedure or a similar procedure), it is ideal to position the prosthesis with 50% of its length above this entry plane including the nadirs of each cusp, and 50% of its length below this plane. That is to say, in some implementations, the entry plane including the nadirs of each cusp ideally bisects the implanted prosthesis. Further, in some implementations, a longitudinal axis of an implanted prosthesis can extend orthogonally relative to the entry plane or at an angle relative to the entry plane. It should be understood that other orientations and positions relative to the cusps and/or plane of the nadirs are possible. Therefore, properly positioning the valve prosthesis currently requires obtaining a radiographic projection by which the nadirs of all aortic root cusps are located in the same plane.

Figure 5A:
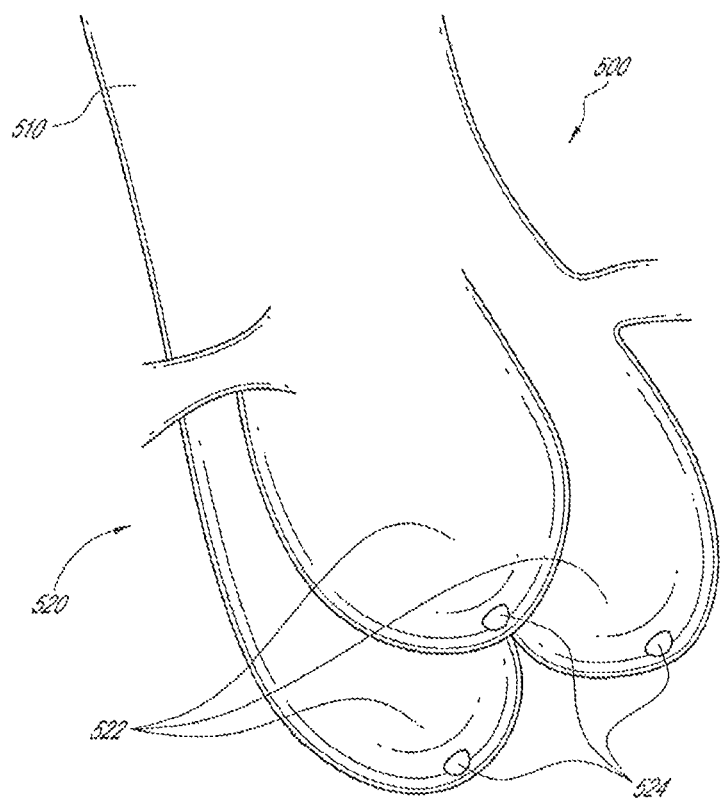
FIGS. 5A-5C schematically depict an example of an aortic root including graphical representations of the nadirs of each cusp.

FIG. 5A schematically depicts an example of a patient's vasculature 500 including an ascending aorta 510 and an aortic root 520. The aortic root 520 includes three cusps 522, which collectively form a tri-cuspid aortic valve. Each cusp 522 includes a nadir 524 that represents the lowest most point of the cusp 522 (e.g., the point that is most distal from the sinotubular junction). The nadirs 524 are graphically represented as discrete tips or ball-type structures in FIGS. 5A-5C for illustrative purposes. However, those having ordinary skill in the art will appreciate that the nadir of an aortic root cusp is not a structure that is discrete or separate from the body of the cusp.

Figure 5B:
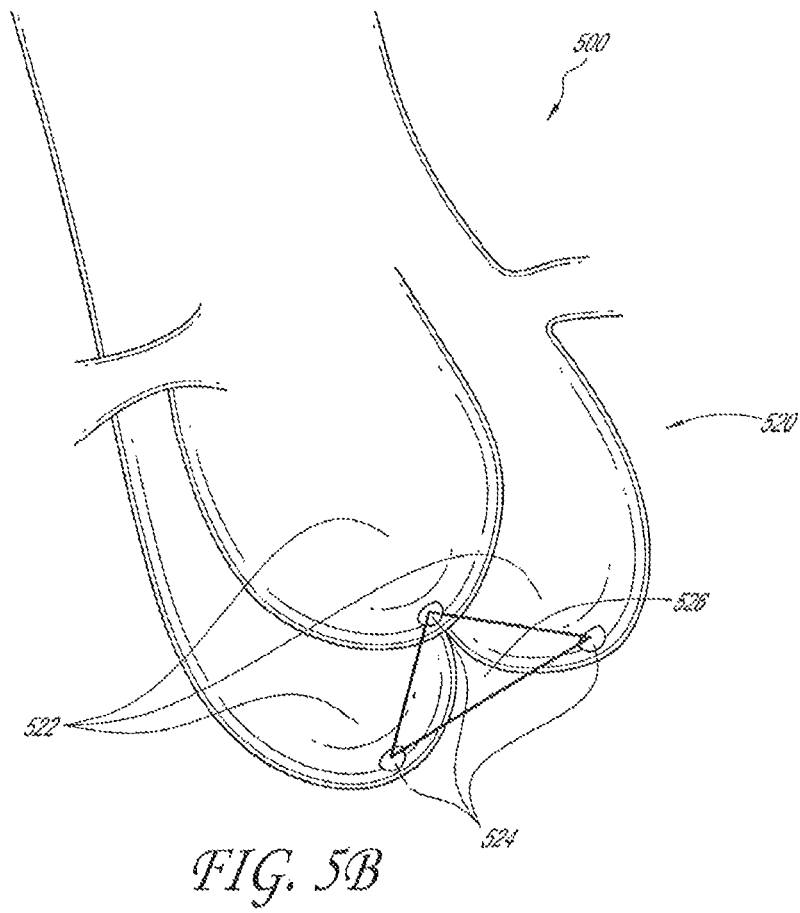
Figure 5C:
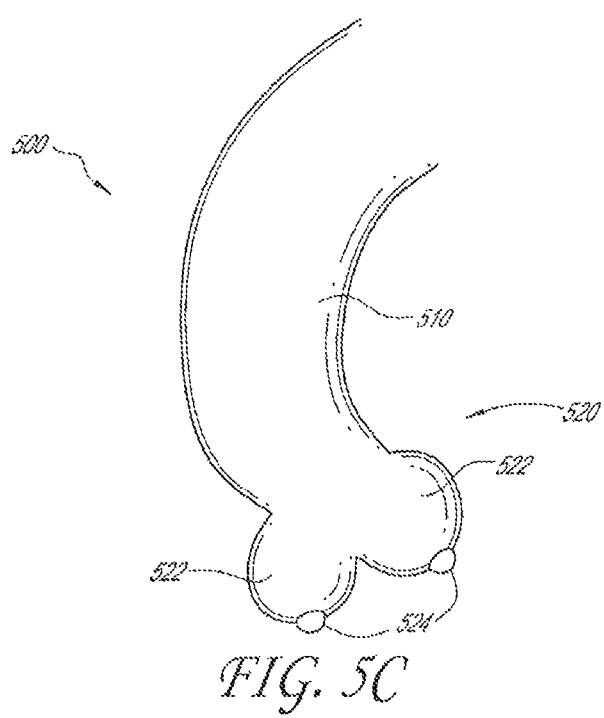

As shown in FIGS. 5B and 5C, locating the entry plane of an aortic root radiographically can be difficult using existing methods, because, among other things, fluoroscopic images are two-dimensional and the aortic valve formed by the cusps 522 is a three-dimensional structure. For example, although FIG. 5B shows the nadirs 524 of each cusp 522, the orientation of the entry plane 526 on which each nadir 524 is disposed cannot clearly be determined from this view. That is to say, the angle at which the entry plane 526 is disposed relative to a longitudinal axis of the aortic root 520 is not readily apparent in the view shown in FIG. 5B. Additionally, FIG. 5C represents a two-dimensional view of the aortic root 520 in which only two of the three nadirs 524 are visible because the visible cusps 522 shield the third nadir 524 from view.

As can be appreciated by reviewing FIGS. 5A-5C, TAVR procedures can require multiple fluoroscopic images and administration of large amounts of contrast material, until a view is obtained in which the entry plane 526 upon which the nadirs 524 of all three cusps 522 (or two cusps in the less common bi-cuspid valve) lie is discernible to a medical professional. A suitable view of a valve can be very difficult to locate without the administration of large amounts of contrast material and multiple fluoroscopic images. These administrations can lead to increased procedural time, increased material costs, increased radiation exposure for the patient, and increased exposure to contrast material, which can lead to renal failure.

FIGS. 6A-7B schematically depict embodiments of a medical device 600, 700 that can be used to visually (e.g., radiographically) locate the entry plane of an aortic root. Such medical devices 600, 700 can be used, for example, during TAVR procedures, to position an aortic valve prosthesis device relative to the entry plane of an aortic root.

To assist in the description of the components of the medical devices described below (see, e.g., FIG. 6A), the following coordinate terms are used: a "longitudinal axis" is substantially parallel to a portion of the medical device, as well as parallel to the lumen or channel of any vasculature in which the medical device is disposed; a "radial axis" is any axis that intersects and lies normal to the longitudinal axis as seen in FIG. 6A (thus, those having ordinary skill in the art will appreciate that each medical device can be described relative to a single longitudinal axis and an infinite number or radial axes); a "longitudinal direction" refers to a direction substantially parallel to the longitudinal axis; a "radial direction" refers to a direction substantially parallel to a radial axis; and "substantially parallel" can refer to two or more lines or directions that do not intersect or that define an angle of about 15° or less at an intersection. For example, in some embodiments, substantially parallel lines or directions can mean lines or directions that do not intersect or that define an angle of about 15°, 14°, 13°, 12°, 11°, 10°, 9°, 8°, 7°, 6°, 5°, 4°, 3°, 2°, 1°, or fewer, at an intersection of the lines or directions.

"Connected" and "coupled," and variations thereof, as used herein, include direct connections, such as being glued or otherwise fastened directly to, on, within, etc. another element, as well as indirect connections where one or more elements are disposed between the connected elements.

"Secured" and variations thereof, as used herein, include methods by which an element is directly secured to another element, such as being glued or otherwise fastened directly to, on, within, etc. another element, as well as indirect means of securing two elements together where one or more elements are disposed between the secured elements.

Movements which are "counter" are movements in an opposite direction. For example, if the medical device is rotated clockwise, rotation in a counterclockwise direction is a movement which is counter to the clockwise rotation. Similarly, if the medical device is moved substantially parallel to the longitudinal axis of the blood vessel in a distal direction, movement substantially parallel to the longitudinal axis in a proximal direction is a counter movement.

Turning now to FIG. 6A, an embodiment of a medical device 600 is schematically illustrated. As illustrated, the medical device 600 can include a catheter body 606 extending longitudinally from a hand piece 604. The catheter body 606 can define a lumen that extends between a distal aperture or opening 608 and the hand piece 604. The hand piece 604 can be coupled to a connector fitting 602 that defines a proximal end of the medical device 600. In some embodiments, the connector fitting 602, the hand piece 604, and the catheter body 606 collectively define a lumen that extends longitudinally through the medical device 600. In this way, fluids (e.g., radiographic dye fluids) and/or other medical devices (e.g., one or more guidewires or transvascular medical devices) can be introduced into a patient through the catheter body 606 by introducing such fluids and/or devices into the medical device 600 via the connector fitting 602 and advancing them through the distal end 608.

With continued reference to FIG. 6A, in some embodiments, the medical device 600 can include a knob or other manipulation element 610 that is slidable within a track or a slot 612 of the catheter body 606. In this way, a user can slide or otherwise manipulate components of the medical device 600 that are disposed within the catheter body 606 by moving the knob 610 within the track 612. For example, as shown in FIG. 6B, in some embodiments, the medical device 600 can include an expandable element 625 that can be positioned at least partially within, and may be movable relative to, the catheter body 606. In some embodiments, the expandable element 625 (not visible in 6A because it is retracted into the catheter body 606) can be manipulated between at least a first configuration (shown in FIG. 6A) and a second configuration (shown in FIG. 6B) by moving the knob 610 to translate the expandable element 625 relative to the catheter body 606 through the distal end 608. In this way, the expandable element 625 can be disposed within the catheter body 606 in the first configuration and can extend through the distal end 608 of the catheter body 606 when in the second configuration. As described in further detail below, the catheter body 606 can be introduced into a patient's vasculature with the expandable element 625 in the first configuration, and the expandable element 625 can be advanced to the second configuration once the distal end 608 of the catheter body 606 is disposed proximate to a specific portion of the patient's vasculature, e.g., an aortic root. In an embodiment, the expandable element 625 can extend about 2 centimeters to about 5 centimeters, such as about 3 centimeters, from the distal end 608 of the catheter body.

Referring now to FIG. 6B, the expandable element 625 can include at least three members 630a, 630b, and 630c. Each member 630 can be biased to move away from the longitudinal axis of the medical device 600 in a radial direction upon exiting the distal end 608 of the catheter body 606. In an embodiment, the members 630 of the expandable element 625 can form a diameter of about 18 millimeters to about 29 millimeters, inclusive. In some embodiments, each member 630 can comprise a flexible material, for example, a metal or metallic alloy having a memory. Contacting intravascular structures with flexible members 630 will have minimal risk of damage to the contacted intravascular structures. In one embodiment, each member 630 comprises a metal alloy including at least nickel and titanium (e.g., Nitinol). In some embodiments, each member 630 can comprise a non-metallic material, for example, a plastic, polymer, rubber, thermoplastic, or other material. In some embodiments, the members 630 can each comprise the same material and in other embodiments, one or more members 630 can comprise a different material from at least one of the other members 630.

Each member 630 can include a distal tip 633 including at least one radiographic marker 635. In some embodiments, the radiographic markers 635 can include radiopaque and/or radiodense materials, for example, gold or platinum. In some embodiments, the radiographic markers 635 can be separate from the members 630 and coupled thereto. In other embodiments, the radiographic markers 635 can be integrally formed with the members 630 and can be distinguished from the remainder of the members by radiodense characteristics.

As illustrated, each radiographic marker 635 can be disposed at the distal most end of its respective tip 633. Each member 630 and tip 633 can extend longitudinally from the distal end 608 of the catheter body 606 to the same degree such that the radiographic markers 635 can define a triangle disposed on a geometric plane (as shown in FIG. 6C). In this way, a view of the medical device 600 where the three radiographic markers 635 are disposed in a common line is indicative of at least one dimension along which the geometric plane extends (e.g., vertically in FIG. 6B).

In some embodiments, the distal tips 633 of each member 630 can be sized and shaped to be complementary to the size and shape of a patient's aortic cusps. For example, the shape of the distal tip 633 can resemble a "pigtail" or J-shape having a curvature that allows the distal tip 633 to engage an aortic cusp within an aortic root. In this way, the distal tips 633 of the three members 630 can each be positioned within the aortic root of a patient such that each tip 633 is disposed in contact with and adjacent to at least one aortic cusp. In such a position, the expandable element 625 can be positioned within a patient's vasculature such that each radiographic member 635 is adjacent to a nadir of a cusp engaged by a corresponding tip 633 of the expandable element 625.

In some embodiments, each member 630 can extend from a common branch or trunk of the expandable element 625. In this way, each member 630 can be secured relative to each other member such that all three members 630 can be manipulated together within a patient's vasculature by rotating a proximal end of the medical device 600. For example, a medical professional can rotate the hand piece 604 with the expandable element 625 in the deployed configuration shown in FIG. 6B until each distal tip 633 sits within the bottom of one of three aortic cusps (not shown).

Turning now to FIG. 7A, another embodiment of a medical device 700 is schematically illustrated. The medical device 700 can include a catheter body 706 extending longitudinally from a hand piece 704. The catheter body 706 can define a lumen that extends between the hand piece 704 and a distal tip 743. The catheter body 706 can resemble a pigtail catheter. Accordingly, in some embodiments, the distal tip 743 can have a rounded pigtail shape. In some embodiments, the hand piece 704 can be coupled to a connector fitting 702 which defines a proximal end of the medical device 700. In some embodiments, the connector fitting 702, the hand piece 704, and the catheter body 706 collectively define a common lumen that extends longitudinally through the medical device 700.

In some embodiments, the distal tip 743 of the catheter body 706 includes one or more apertures or ports 747. The ports 747 can be fluidly coupled to the lumen of the catheter body 706. In this way, the ports 747 can provide for ingress and/or egress of fluids between the lumen of the catheter body 706 and a patient's vasculature. As such, in some embodiments, the ports 747 can optionally be utilized to introduce radiographic dyes into a patient. Additionally, the ports 747 can optionally be used to determine a fluidic pressure within a portion of a patient's vasculature and/or to aspirate fluid from the patient via the catheter body 706.

In some embodiments, the distal tip 743 can also include at least one radiographic marker 745 disposed at or near the distal most end of the tip 743. The at least one radiographic marker 745 can include any suitable radiopaque and/or radiodense material(s), which enable the distal tip 743 to be viewed radiographically when the distal tip 743 is disposed within a patient's vasculature (e.g., within or proximate to a patient's aortic root). In some embodiments, the radiographic marker 745 can be separate from the catheter body 706 and coupled thereto. In other embodiments, the radiographic markers 745 can be integrally formed with the catheter body 706 and can be distinguished from the remainder of the catheter body 706 by radiodense characteristics.

With continued reference to FIG. 7A, in some embodiments, the medical device 700 can include a knob or other manipulation element 710 that is slidable within a track or a slot 712 of the catheter body 706. Thus, a user can slide or otherwise manipulate components of the medical device 700 that are disposed within the catheter body 706 by moving the knob 710 within the track 712.

In some embodiments, the medical device 700 can also include an opening 708 disposed between the distal tip 743 and the hand piece 704. For example, as shown in FIG. 7B, in some embodiments, the medical device 700 can include an expandable element 725 that can be positioned at least partially within the catheter body 706. In some embodiments, the expandable element 725 can be manipulated between at least a first configuration (shown in FIG. 7A) and a second configuration (shown in FIG. 7B) by moving the knob 710 so as to translate the expandable element 725 relative to the catheter body 706 and through the opening 708. In this way, the expandable element 725 can be disposed within the catheter body 706 in the first configuration and can extend through the opening 708 of the catheter body 706 when in the second configuration. In use, the catheter body 706 can be introduced into a patient's vasculature with the expandable element 725 in the first configuration and the expandable element 725 can be advanced to the second configuration once the distal tip 743 of the catheter body 706 is disposed proximate to a specific portion of the patient's vasculature, e.g., an aortic root.

Referring now to FIG. 7B, the expandable element 725 can include at least two members or struts 751a and 751b. Each member 751 can be biased to expand away from the longitudinal axis of the medical device 700 in a radial direction upon exiting the opening 708 of the catheter body 706. As such, the distal end 753 of each member 751 can be offset radially from the distal tip 743. In some embodiments, each member 751 can comprise a rigid material, for example, a metal or metallic alloy having a memory. In one embodiment, each member 751 comprises a metal alloy including at least nickel and titanium. In some embodiments, each member 751 can comprise a less rigid material, for example, a plastic, polymer, rubber, thermoplastic, or other material. In some embodiments, the members 751 can each comprise the same material and in other embodiments, one or more members 751 can comprise a different material from at least one of the other members 751.

Each member 751 can include at least one radiographic marker 755 coupled to the distal end 753. In some embodiments, the radiographic markers 755 can have the same or similar radiodense characteristics as the at least one radiographic marker 745 of the distal tip 743. In this way, all three radiographic markers 755a, 745, and 755b illustrated in FIG. 7B can be simultaneously viewed radiographically by a user, for example, a medical professional.

Still referring to FIG. 7B, all three radiographic markers 755a, 745, and 755b can be offset longitudinally at the same distance from the opening 708. In this way, the three radiographic markers 755a, 745, and 755b can define a triangle disposed on a geometric plane (as shown in FIG. 7C). As a result, all three radiographic markers 755a, 745, and 755b form a common line segment indicative of at least one dimension along which the geometric plane extends when viewed from the angle illustrated in FIG. 7B. Thus, the medical device 700 can be used to indicate one direction that a geometric plane including all three markers extends along by aligning the radiographic markers 755a, 745, and 755b as illustrated.

In some embodiments, the distal tip 743 and the ends 753 can be sized and shaped to be complementary to the size and shape of a patient's aortic cusps. For example, the shape of the distal tip 743 can resemble a "pigtail" and the ends 753 can resemble a J-shape. In some embodiments, the distal tip 743 and the ends 753 have a curvature that allows for the structures to engage an aortic cusp within an aortic root. In this way, the distal tip 743 and the ends 753 can each be positioned within the aortic root of a patient such that each structure is disposed in contact with and adjacent to at least one aortic cusp. In such a position, the expandable element 725 can be positioned within a patient's vasculature such that each radiographic member 745 and 755 is adjacent to a nadir of a cusp. Thus, the radiographic markers 755a, 745, and 755b can be used to locate the common plane of three separate points (e.g., three nadirs of aortic cusps) in three dimensions by associating each marker with one of the three points and then finding a view that positions the three markers in a line (as shown in FIG. 7B). Accordingly, as discussed below, the medical devices 600, 700 of FIGS. 6A-7B can be especially useful in positioning an aortic valve prosthesis relative to an aortic root, for example, during a TAVR procedure. In use, the expandable elements of the medical devices 600, 700 of FIGS. 6A-7B are not extended through the aortic valve into a ventricle lumen.

Turning now to FIGS. 8A-8F, an example process of positioning an aortic valve prosthesis 814 relative to an aortic root 820 is schematically depicted. Although the example process is discussed with reference to the medical device 600 of FIGS. 6A and 6B, those having ordinary skill in the art will appreciate that the aortic valve prosthesis 814 can be positioned using any of the embodiments of medical devices disclosed herein.

FIG. 8A illustrates the medical device 600 with the expandable member 625 extended from the distal aperture 608 of the catheter body 606 within the aortic root 820 of the patient. In this configuration, the distal tips 633 of the medical device 600 are expanded radially from the longitudinal axis of the medical device such that the radiographic markers 635 are offset longitudinally from the distal aperture 608 to the same degree. In some embodiments, the proximal end of the catheter body 606 can be disposed outside of the patient's body to allow a medical professional to manipulate the medical device relative to the patient's vasculature (e.g., by gripping the hand piece illustrated in FIGS. 6A and 6B). Thus, the distal tips 633 can be manipulated to engage the cusps 822 such that the radiographic markers 635 are disposed adjacent and proximate to the nadir 824 of each cusp 822.

Turning now to FIG. 8B, with the radiographic markers 635 disposed near the nadirs 824, the radiographic imaging device (e.g., fluoroscopy gantry equipment) can be manipulated relative to the patient until the radiographic markers 635 are disposed in a line segment as shown. As discussed above, because each nadir 824 is disposed on a common entry plane 826 to the aortic root 820, such a line indicates one dimension along which the entry plane 826 extends. Accordingly, the identified dimension of the entry plane 826 can be utilized in positioning the aortic valve prosthesis 814.

FIG. 8C illustrates a second medical device 810 introduced into the aortic root 820 along with the medical device 600. The medical device 810 includes a catheter body 812, a guidewire 819, an inflation lumen 818, an inflatable balloon 816, and the aortic valve prosthesis 814. In use, the medical device 810 can be advanced through the patient's vasculature over the guidewire 819 until the distal end of the catheter body 812 is disposed proximal to the aortic root 820. From this position, the aortic valve prosthesis 814 can be advanced longitudinally from the catheter body 812 over the inflatable balloon 816 until the aortic valve prosthesis 814 is disposed between the cusps 822 of the aortic valve.

As discussed above, it can be desirable to implant the aortic valve prosthesis 814 with about 50% of its longitudinal length positioned above the entry plane 826 defined by the nadirs 824 of each cusp 822 and with about 50% of the longitudinal length of the aortic valve prosthesis positioned below the entry plane 826. Such a "50/50" placement can provide for several advantages. For example, placing the aortic valve prosthesis 814 with about 50% of its longitudinal length positioned above the entry plane 826 defined by the nadirs 824 of each cusp 822 and with about 50% of the longitudinal length of the aortic valve prosthesis positioned below the entry plane 826 can provide for adequate grip or engagement between the aortic valve prosthesis and the patient. Further, if the aortic valve prosthesis 814 is placed too high, the cusps 822 may be splayed out such that the aortic valve prosthesis 814 will disengage and/or translate relative to the entry plane 826. On the other hand, if the aortic valve prosthesis 814 is placed too low, the aortic valve prosthesis 814 may impinge on the anterior leaflet of a mitral valve and/or press against the septum, which can cause electrical conduction problems. As used herein, about 50% can be any percentage between and including 30% and 70%, for example, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, and 70%. In other words, it can be desirable to position the aortic valve prosthesis 814 relative to the aortic root 820 such that the entry plane 826 bisects the aortic valve prosthesis 814, as shown in the example of FIG. 8D.

Turning now to FIG. 8E, once the aortic valve prosthesis 814 is properly positioned relative to the aortic root 820, the medical device 600 can be removed from the vicinity to allow for the expansion of the inflatable balloon 816, in some embodiments. Thus, the medical device 600, and other embodiments disclosed herein, can be used to properly position an aortic valve prosthesis relative to an aortic root without the use of software and/or while minimizing, reducing, or eliminating the use of harmful dye injections.

Still referring to FIG. 8E, after the medical device 600 is withdrawn, the inflatable balloon 816 can be expanded via the inflation lumen 818 to expand the aortic valve prosthesis 814 radially until the aortic valve prosthesis contacts or engages the circumference of the aortic root 820. In this way, the diseased cusps 822 can be urged away from each other and positioned radially outside of the aortic valve prosthesis 814. As shown in FIG. 8F, the expanded aortic valve prosthesis 814 can be left within the aortic root 820 after the medical device 810 is withdrawn to treat the diseased aortic valve. Examples of suitable aortic valve prostheses 814 include the SAPIEN transcatheter aortic valve and the COREVALVE transcatheter aortic valve, each of which include tri-cuspid passive valves (not shown) disposed within a tubular stent.

While the process described with reference to FIGS. 8A-8F utilize two separate medical devices (e.g., the medical device 810 and the medical device 600), it should be understood that a single medical device can be configured and provided for locating the entry plane and providing a lumen for introducing and deploying an aortic valve prosthesis. Additionally, while the depicted examples of entry plane locating devices use a single device (e.g., catheter) from which the three pigtails or J-shaped devices project, it should be understood that multiple devices (e.g., catheters) can be used as well, each with one or more projections and/or tips. Moreover, any of the medical devices disclosed herein (e.g., the medical devices 600, 700, and/or 810) can provided to a medical professional with other medical devices, for example, in a kit. Those having ordinary skill in the art will understand that while pigtail and J-shaped tips are depicted, it should be understood that other configurations can be used. Preferably, those configurations permit the positioning of the tip with a radiographic marker that can be visualized or detected at the bottom of the cusps in order to more efficiently or simply identify the entry plane of the cusps.

While positioning of an aortic valve prosthesis (e.g., a replacement valve) is described where the valve has about 50% of its length on each side of the plane, it should be understood that the exact placement can be in any manner (or percentage) according to a particular procedure and device that is being placed across the valve cusps. The percentage described is not meant to be limiting, but is one example that is desired in some procedures. Also, while the term "catheter" is used herein, it should be understood that other devices can be utilized in order to introduce the systems, devices and projections described herein into position for an aortic procedure. Finally, while the systems and devices have been described in connection with aortic replacement procedures, it should be understood that the systems and devices can be used in other medical procedures where detection or determination of the plane of a region is desired.

The foregoing description details certain embodiments of the aortic valve positioning systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the drawings can be combined, interchanged, or excluded from other embodiments.

With respect to the use of any plural and/or singular terms herein, those having skill in the art can translate from the plural to the singular and/or from the singular to the plural as is appropriate to the context and/or application. The various singular/plural permutations can be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite devices "a" or "an" limits any particular claim containing such introduced claim recitation to embodiments containing only one such recitation, even when the same claim includes the introductory phrases "one or more" or "at least one" and indefinite devices such as "a" or "an" (e.g., "a" and/or "an" should typically be interpreted to mean "at least one" or "one or more"); the same holds true for the use of definite devices used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The Abstract is provided to allow the reader to quickly ascertain the nature of the technical disclosure. It is submitted with the understanding that it will not be used to interpret or limit the scope or meaning of the claims.

In the event of inconsistent usages between this document and any document so incorporated by reference, the usage in this document controls.

What is claimed is:

1. A medical device, comprising:
    a body member extending along a longitudinal axis and defining a lumen having an opening;
    an expandable element, at least partially disposed within the lumen, extending from a proximal end portion to a distal end portion and including a plurality of flexible members and radiographic markers, a distal tip portion of each flexible member including a pigtail shape or a J-shape having a distal most curvature to which a radiopaque marker is disposed or integrated; and
    a knob engaged with the proximal end portion of the expandable element, the knob, when actuated, configured to move the expandable element back and forth between a first configuration, in which the plurality of radiographic markers are disposed within the lumen, and a second configuration, in which the plurality of radiographic markers are disposed outside of the lumen,
    wherein the plurality of radiographic markers pass through the opening of the body member when the expandable element moves between the first configuration and the second configuration.

2. The medical device of claim 1, wherein the plurality of radiographic markers includes three radiographic markers.

3. The medical device of claim 2, wherein the three radiographic markers are equally radially offset from the longitudinal axis of the body member or equally longitudinally spaced from the opening of the body member when the expandable element is at the second configuration.

4. The medical device of claim 2, wherein the three radiographic markers form a common line, indicative of at least one dimension along an entry plane to an aortic root, when the expandable element is at the second configuration.

5. The medical device of claim 2, wherein the plurality of flexible members includes three flexible members.

6. The medical device of claim 1, wherein the body member includes a distal tip portion, and wherein the opening is longitudinally offset from the distal tip portion along the body member.

7. The medical device of claim 6, further comprising a radiographic marker coupled to or integrated with the distal tip portion of the body member.

8. The medical device of claim 7, wherein the plurality of flexible members includes two flexible members.

9. The medical device of claim 8, wherein the radiographic markers of the two flexible members and the radiographic marker of the distal tip portion of the body member are equally radially offset from the longitudinal axis of the body member when the expandable element is at the second configuration.

10. The medical device of claim 8, wherein the radiographic markers of the two flexible members and the radiographic marker of the distal tip portion of the body member form a common line, indicative of at least one dimension along an entry plane to an aortic root, when the expandable element is at the second configuration.

11. The medical device of claim 8, wherein the distal tip portion of the body member is sized and shaped to complement and be received by an aortic valve cusp.

12. The medical device of claim 11, wherein the distal tip portion of the body member includes a pigtail shape or a J-shape.

13. The medical device of claim 6, wherein the distal tip portion of the body member includes at least one port disposed in fluid communication with the lumen.

14. The medical device of claim 1, wherein the plurality of flexible members are configured such that rotational manipulation, applied at the proximal end portion of the expandable member post-implant, leads the radiographic marker of each flexible member to a location at or near a lowest point of a respective aortic valve cusp.

15. The medical device of claim 1, wherein the knob is disposed at a proximal end portion of the body member and is movable within a track or slot in a wall of the body member.

16. A method comprising:
    introducing at least three radiographic markers into a vessel;
    advancing each of the at least three radiographic markers to one of a plurality of aortic valve cusps, including moving an expandable element from a first configuration, in which at least two of the radiographic markers are disposed within a body member lumen, to a second configuration, in which the at least two radiographic markers are disposed outside of the body member lumen;
    with the expandable element at the second configuration, defining a geometric plane at the aortic valve cusps using the at least three radiographic markers; and
    manipulating a radiographic imaging device configured to produce a radiographic image, wherein the manipulating includes producing a radiographic image in which the at least three radiographic markers are disposed in a common line segment.

17. The method of claim 16, wherein defining the geometric plane at the aortic valve cusps includes disposing each radiographic marker in direct contact with a nadir of a respective aortic valve cusp.

18. The method of claim 16, wherein providing the radiographic image in which the at least three radiographic markers are disposed in the common line segment includes identifying at least one dimension of the geometric plane.

19. The method of claim 16, further comprising advancing an aortic valve prosthesis through the vessel and positioning the aortic valve prosthesis adjacent the aortic valve cusps.

20. The method of claim 19, wherein positioning the aortic valve prosthesis includes positioning a first portion of the aortic valve prosthesis on a first side of the geometric plane and positioning a second portion of the aortic valve prosthesis on a second side of the geometric plane, which is opposite to the first side.

21. The method of claim 16, wherein moving the expandable element from the first configuration to the second configuration includes moving a knob engaged with the proximal end portion of the expandable element.

22. The method of claim 21, wherein moving the knob includes rotating the knob.

* * * * *